(12) United States Patent
Vodyanoy et al.

(10) Patent No.: US 7,138,238 B2
(45) Date of Patent: Nov. 21, 2006

(54) LIGAND SENSOR DEVICES AND USES THEREOF

(75) Inventors: Vitaly Vodyanoy, Auburn, AL (US); Alexandre M. Samoylov, Auburn, AL (US); Tatiana I. Samoylova, Auburn, AL (US); Suram T. Pathirana, Sunnyvale, CA (US)

(73) Assignee: Auburn University, Auburn, AL (US)

( * ) Notice: Subject to any disclaimer, the term of this patent is extended or adjusted under 35 U.S.C. 154(b) by 496 days.

(21) Appl. No.: 10/068,570

(22) Filed: Feb. 6, 2002

(65) Prior Publication Data

US 2003/0040466 A1 Feb. 27, 2003

Related U.S. Application Data

(60) Provisional application No. 60/266,755, filed on Feb. 6, 2001.

(51) Int. Cl.
*G01N 33/53* (2006.01)
(52) U.S. Cl. .................. 435/7.1; 435/7.2; 435/69.7; 436/71; 436/86; 422/105
(58) Field of Classification Search ............... 435/7.1, 435/69.7, 7.2; 436/86, 71; 422/105
See application file for complete search history.

(56) References Cited

U.S. PATENT DOCUMENTS

| | | | |
|---|---|---|---|
| 4,242,096 A | 12/1980 | Oliveira et al. | |
| 4,314,821 A | 2/1982 | Rice | |
| 4,554,076 A | 11/1985 | Speaker | |
| 4,735,906 A | 4/1988 | Bastiaans | |
| 4,940,516 A | 7/1990 | Wegmann et al. | |
| 5,019,451 A | 5/1991 | Lando | |
| 5,102,798 A | 4/1992 | Guiseppi-Elie | |
| 5,120,809 A | 6/1992 | Lupo et al. | |
| 5,510,481 A | 4/1996 | Bednarski et al. | |
| 5,580,612 A | 12/1996 | Hickel et al. | |
| 5,622,699 A | 4/1997 | Ruoslahti et al. | |
| 6,165,335 A | 12/2000 | Lennox et al. | |
| 6,630,358 B1 * | 10/2003 | Wagner et al. | ............... 436/518 |

FOREIGN PATENT DOCUMENTS

| EP | 0 637 384 B1 | 10/1996 |
|---|---|---|
| WO | WO 87/00347 | 1/1987 |
| WO | WO 00/62351 | 10/2000 |

OTHER PUBLICATIONS

Birkert et al. Analytical Biochemistry 2000 282: 200.*
Ahluwalia, A., et al., "A Comparative Study of Protein Immobilization Techniques for Optical Immunosensors," *Biosensors and Bioelectronics,* 1991, pp. 207-214, vol. 7, Elsevier Science Publishers Ltd.

Barry, M., et al., "Toward Cell-Targeting Gene Therapy Vectors: Selection of Cell-Binding Peptides from Random Peptide-Presenting Phage Libraries," *Nature Medicine,* 1996, pp. 299-305, vol. 2(3).
Cwirla, S., et al., "Peptides on Phage: A Vast Library of Peptides for Identifying Ligands", *Proceedings of the National Academy of Science.* USA, Aug. 1990, pp. 6378-6382, vol. 87.
Decker, J., et al., "Characterization of a Human Pancreatic Secretory Trypsin Inhibitor Mutant Binding to *Legionella pneumophila* as Determined by a Quartz Crystal Microbalance," *Journal of Immunological Methods,* 2000, pp. 159-165, vol. 233, Elsevier Science Publishers, B.V.
Delvin, J., et al., "Random Peptide Libraries: A Source of Specific Protein Binding Molecules," *Science,* 1990, pp. 404-406, vol. 249.
Ebato, H., et al., "Investigation of Specific Binding of Antifluorescyl Antibody and Fab to Fluroescein Lipids in Langmuir—Blodgett Deposited Films Using Quartz Crystal Microbalance Methodology," *Analytical Chemistry,* 1994, pp. 1683-1689, vol. 66(10).
Gizeli, E. and Lowe, C., "Immunsensors," *Analytical Biotechnology,* 1996, pp. 66-71, vol. 7.
Feero, W. and Hoffman, E., "Toward Systemic Gene Delivery for Duchenne Muscular Dystrophy: Transferrin as a Muscle Targeting Ligand," *Neurology,* 1996, p. A390, vol. 46(2).
Hengerer, A., et al., "Quartz Crystal Microbalance (QCM) as a Device for the Screening of Phage Libraries", *Biosensors and Bioelectronics,* 1999, pp. 139-144, vol. 14, Elsevier Science S.A.
Hengerer, A., et al., "Determination of Phase Antibody Affinities to Antigen by a Microbalance Sensor System," *BioTechniques,* 1999, pp. 956-963, vol. 26(5).
Pasqualini, R. and Rousiahti, E., "Organ Targeting *In Vivo* Using Phage Display Peptide Libraries," *Nature,* 1996, pp. 364-366, vol. 380.
Petty, M., "Application of Multilayer Films to Molecular Sensors: Some Examples of Bioengineering at the Molecular Level," *Journal of Biomedical Engineering,* 1991, pp. 209-214, vol. 13.
Polgren, A., et al., "Identification of Muscle Homing Sequences by Using Phase Display Libraries of Peptides," 0-155, p. 77.
Russell, S., "Peptide-Displaying Phages for Targeted Gene Delivery?", *Nature Medicine,* 1996, pp. 276-277, vol. 2(3).
Schumacher, T., et al., "Identification of D-Peptide Ligands Through Mirror-Image Phage Display," *Science,* 1996, pp. 1854-1857, vol. 271.

(Continued)

*Primary Examiner*—Long V. Le
*Assistant Examiner*—Jacob Cheu
(74) *Attorney, Agent, or Firm*—Alston & Bird LLP

(57) ABSTRACT

Methods and compositions for evaluating the affinity of one or more ligands of interest are provided. In particular, a ligand sensor device (LSD) comprising a sensor coupled to a peptide of interest is provided. Assays using the LSD allow detection of ligand-peptide interactions directly in tissue samples and thus provide an in vitro assay to characterize peptide ligands. The LSD and assays find particular use in characterizing cell-specific peptides isolated from in vivo screening in animals to determine their suitability for use in human therapy.

6 Claims, 6 Drawing Sheets

OTHER PUBLICATIONS

Smith, G. and Evans, T., "Optimization of Thermal Performance of Langmuir-Blodgett Film Pyroelectric Devices," *Thin Solid Films*, 1987, pp. 7-13, vol. 146, Elsevier Sequoia, Netherlands.

Smith, G., et al., "Pyroelectric Activity in Non-Centrosymmetric Langmuir-Blodgett Multilayer Films," *Thin Solid Films*, 1985, pp. 125-134, vol. 132, Elsevier Sequoia, Netherlands.

Suleiman, A. and Guilbaut, G., "Recent Developments in Piezoelectric Immunosensors," *Analyst*, 1994, pp. 2279-2282, vol. 119.

Gau, J., et al., "A MEMS Based Amperometric Detector for *E. coli* Bacteria Using Self-Assembled Monolayers," *Biosensors & Bioelectronics*, 2001, pp. 745-755, vol. 16.

Luppa, P.B., et al., "Immunosensors—Principles and Applications to Clinical Chemistry," *Clinica Chimica Acta*, 2001, pp. 1-26. vol. 314.

Pasqualini, R., "Vascular Targeting with Phage Peptide Libraries," *The Quarterly Journal of Nuclear Medicine*, 1999, pp. 159-162, vol. 43.

Pathirana, S.T., et al., "Rapid and Sensitive Biosensor for *Salmonella*," *Biosensors & Bioelectronics*, 2000, pp. 135-141, vol. 15.

Samoylova, T.I., and Smith, B.F., "Elucidation of Muscle-Binding Peptides by Phage Display Screening," *Muscle & Nerve*, 1999, pp. 460-466, vol. 22(4).

Ahlers, M. et al. "Specific Recognition and Formation of Two-Dimensional Streptavidin Domains in Monolayers: Applications to Molecular Devices," *Thin Solid Films*, 1989, pp. 93-99, vol. 180(1-2).

Samoylov, A. M., et al. "Peptide Biosensor for Recognition of Cross-Species Cell Surface Markers," *Journal of Molecular Recognition*, 2002, pp. 197-203, vol. 15(4).

Samoylov, A. M., et al. "Recognition of Cell-Specific Binding of Phage Display Derived Peptides Using an Acoustic Wave Sensor," *Biomolecular Engineering*, 2002, pp. 269-272, vol. 18(6).

Samoylov, A. M., et al. "Recognition of Cell-Surface Markers with Peptide Biosensors," *Biophysical Journal*, 2001, p. 315a, vol. 80(1) part 2.

* cited by examiner

SEQUENCE LISTING

```
<160> NUMBER OF SEQ ID NOS: 3

<210> SEQ ID NO 1
<211> LENGTH: 7
<212> TYPE: PRT
<213> ORGANISM: Artificial Sequence
<220> FEATURE:
```

```
-continued

<223> OTHER INFORMATION: identified by phage screening

<400> SEQUENCE: 1

Ala Ser Ser Leu Asn Ile Ala
 1               5

<210> SEQ ID NO 2
<211> LENGTH: 5
<212> TYPE: PRT
<213> ORGANISM: Artificial Sequence
<220> FEATURE:
<223> OTHER INFORMATION: spacer

<400> SEQUENCE: 2

Gly Gly Gly Ser Lys
 1               5

<210> SEQ ID NO 3
<211> LENGTH: 12
<212> TYPE: PRT
<213> ORGANISM: Artificial Sequence
<220> FEATURE:
<223> OTHER INFORMATION: sequence comprising artificial sequence of SEQ
      ID NO:1 and spacer of SEQ ID NO:2

<400> SEQUENCE: 3

Ala Ser Ser Leu Asn Ile Ala Gly Gly Gly Ser Lys
 1               5                   10
```

LIGAND SENSOR DEVICES AND USES THEREOF

CROSS-REFERENCE TO RELATED APPLICATIONS

This Application claims the benefit of U.S. Provisional Application No. 60/266,755, filed Feb. 6, 2001, which disclosure is herein incorporated.

FEDERAL FUNDING DISCLOSURE

This work was supported partially by a grant from DARPA MDA972-00-1-0011.

FIELD OF THE INVENTION

The invention relates to sensors for the detection of ligands of peptides of interest and uses thereof.

BACKGROUND OF THE INVENTION

Often the successful treatment of disorders and diseases is hampered by a lack of specificity. Pharmaceuticals which are very effective for treating a disorder in one organ or tissue may have undesirable effects in other tissues and thus limit the usefulness of the treatment. In this way, the effectiveness of drugs and therapeutic genes depends on tissue-specific delivery. One prospect for achieving tissue-specific delivery of drugs is the use of ligands which bind to specific cell types. However, the development of tissue-specific ligands for many differentiated tissues is limited by a lack of information on their cell-specific surface receptors. One solution to this problem is the selection of ligands using phage display libraries. This approach requires no prior knowledge of the target cell receptor expression and function (Barry et al. (1996) *Nature Med.* 2:299–305). The screening of M13 phage display peptide libraries was first employed to select cell-specific ligands in vitro, and it has also proven useful for the rapid in vivo discovery of small molecule ligands specific to various organs and tissues (Pasqualini and Ruoslahti (1996) *Nature* 380:364–366; Pasqualini (1999) *Q. J. Nucl Med.* 43:159–162; Samoylova and Smith (1999) *Muscle & Nerve* 22:460–466). Peptides identified via phage display screening were used to achieve selective delivery of the cytotoxic drug doxorubicin to tumors, thereby decreasing side effects from the drug's effects on untargeted organs and systems (Arap et al. (1998) *Science* 279:377–380). Specific gelatinase inhibitors identified from phage display peptide libraries can prevent the migration of human endothelial cells and tumor cells, thereby reducing tumor growth in mice bearing human tumors (Koivunen et al. (1999) *Nat. Biotechnol.* 17:768–774). Phage display screening can also be used to improve the properties of known proteins or nucleic acids. For example, the selectivity of intravenously administered adenoviral vectors was improved significantly by the insertion of phage derived peptide motifs into the H1 loop of the fiber knob protein (Reynolds et al. (1999) *Gene Ther.* 6:1336–1339).

Thus, peptides generated by phage display may have both therapeutic and diagnostic utility. They can be useful for the development of gene therapy vectors or drugs targeting various organs and tissues. However, while the in vivo phage display screening protocol has been successful in identifying tissue-specific ligands in mice and dogs, in vivo screening requires euthanasia and thus cannot be applied to humans. Thus, there remains a need for compositions and methods for the identification of interspecies cell-specific peptides, particularly for use in humans. Identification of interspecies cell-specific peptides by selection in multiple animal species and then determination of their affinity to human tissues would allow isolation of tissue-specific molecules that may be used as targeting ligands in gene/drug therapy protocols.

"Biosensors" have been reported in the literature, but the reported devices have low sensitivity or long response times. Decker et al. ((2000) *J. Immunol. Methods* 233:159–165) reported that more than 90 minutes were needed to measure phage binding by peptide fragments immobilized by biotin/streptavidin coupling. Hengerer et al. ((1999) *Biotechniques* 26: 956–60, 962, 964) reported binding of phage antibodies to antigen immobilized on a quartz crystal microbalance with a time constant of about 100 min. These long response times are not compatible with rapid screening and make large-scale screening unwieldy. Therefore, there remains a need for a biosensor which can rapidly detect specific proteins.

SUMMARY OF THE INVENTION

The invention provides a ligand sensor device which comprises an acoustic wave device coupled to a peptide of interest. The invention allows detection of ligand-peptide interactions directly in tissue samples. In this manner, the invention provides an in vitro assay to examine the cross-species properties of peptide ligands isolated in in vivo phage-display screening and thus provides an assay for the ligands specific to various organs, tissues, and cell types.

DETAILED DESCRIPTION OF THE INVENTION

Figure 1:
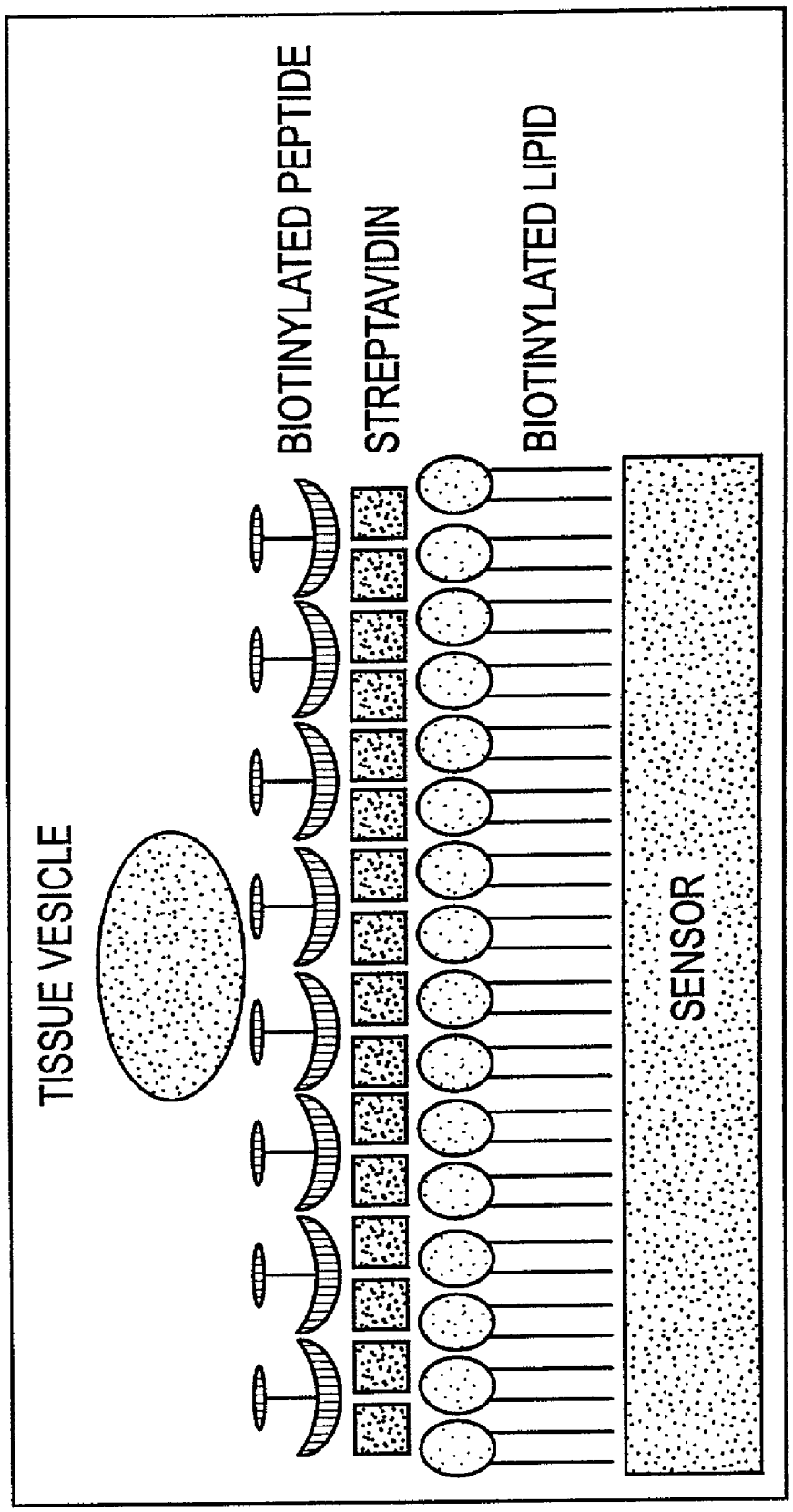
FIG. 1 shows a diagram of an embodiment of the ligand sensor device (LSD) wherein the peptide of interest is coupled to the sensor via a coupling composition layer comprising streptavidin. In the embodiment shown, a Langmuir-Blodgett film comprising biotinylated lipid has been deposited on the sensor. In addition, the peptide of interest has been biotinylated. The addition of streptavidin results in molecular self-assembly whereby the peptide of interest is coupled to the sensor.

Methods and compositions for evaluating the affinity of one or more ligands of interest are provided. In particular, ligand sensor devices are provided, as well as assays using ligand sensor devices. The ligand sensor device (LSD) comprises a device coupled sensor coupled to a peptide of interest. The LSD allows detection of ligand-peptide interactions directly in tissue samples. In this manner, the LSD provides an in vitro assay that can be used to examine the cross-species properties of peptide ligands isolated in in vivo phage-display screening and thus provides an assay for the rapid discovery of small molecule ligands specific to various organs, tissues, and/or species. The LSD and assays of the invention are useful in the isolation and identification of tissue-specific molecules that can be used to target various compounds or molecules in gene and/or drug therapy protocols. The LSD and assays find particular use in characterizing cell-specific peptides isolated from in vivo screening in animals to determine their suitability for use in human therapy.

Peptides of interest can be determined which are capable of preferentially or specifically binding any type of tissue cells including muscle, brain, liver, and the like. Peptides of interest can also be determined which are capable of preferentially or specifically binding to a tissue or cell type which is abnormal due to disease or disorder; for example, peptides of interest may bind preferentially to tumor cells. Based on the selective binding protocols, peptides which are tissue-type specific or alternatively which are capable of binding to different cells can be determined. In the same manner, the peptides may be species independent, that is, the peptides bind to the tissue type or cell type from any mammalian species. Alternatively, the peptides may be species specific. By species-specific is intended that peptides are specific for tissue cells (e.g., liver) from a particular species and will not bind to the same tissue cells from another species. Therefore, the peptides may be characterized by tissue specificity and by species specificity. Mammalian species of interest include, but are not limited to human, rat, dog, chimpanzee, etc.

Multiple tissue targets can be utilized to select for specific binding peptides. Peptides can be selected against differentiated cell lines from any mammal, as well as against primary tissue samples from mammals. Peptides of interest may bind specifically or preferentially to a particular cell type. That is, a peptide of interest may bind exclusively to a particular cell or tissue type or it may show greater binding to that cell or tissue type compared to other cell or tissue types. For example, a peptide of interest may exhibit at least three-fold, five-fold, preferably ten-fold, more preferably greater than ten-fold binding affinity for the selected cells or tissue, which may be from a particular species. It is understood that the binding of a peptide of interest to a particular tissue may be affected by the number of ligands or binding sites to which the peptide binds as well as the affinity of the peptide for the ligand. Thus, a peptide may bind murine and feline muscle ligands with the same affinity, but if there are fewer ligands present in feline muscle, the overall binding may be decreased relative to murine muscle.

Methods are available in the art for the determination of peptides of interest. Such methods include selection from a bacteriophage library which expresses random peptides, mirror image phage display to isolate naturally-occurring L-enantiomers in a peptide library, and the like. See, for example, Barry et al. (1996) *Nature Medicine* 2:299–305; Schumacher et al. (1996) *Science* 271:1854–1857; Pasqualini et al. (1996) *Nature* 380:364–366; U.S. Pat. No. 6,329,501, issued Dec. 11, 2001, and the references cited therein, herein incorporated by reference. Peptides of interest are identified by methods known in the art or as discussed in copending applications App. Ser. No. 09/947,137, filed Sep. 5, 2001, and App. Ser. No. 09/438,150, filed Nov. 10, 1999, herein incorporated by reference. Thus, peptides of interest need not be identified by the in vivo phage display screening method, but may be known in the art or produced using other techniques. While many embodiments involve peptides identified by in vivo screening, it is recognized that other molecules may be useful in the methods and compositions of the invention. Such molecules include organic chemicals, modified peptides, proteins such as antibodies, antibody fragments, and the like.

Peptides of interest can be determined from phage libraries which have been used to select random peptides that bind single proteins. See, Barry et al. (1996) *Nature Medicine* 2:299–305; Devlin et al. (1990) 249:404–406; Cwirla et al. (1990) *Proc. Natl. Acad. Sci. USA* 87:6378–6382; and the references cited therein. In this manner, peptide libraries can be constructed utilizing a number of random amino acids. The random amino acids are fused to the amino terminus of a phage protein and expressed as a bacteriophage library. See, Barry et al. (1996) *Nature Medicine* 2:299–305, herein incorporated by reference. The phage is incubated with the cells of interest at different temperatures generally about 4° C. and about 37° C. After repeated selection rounds, peptides which exhibit a higher affinity for the cells of interest are isolated. Methods for preparing libraries containing diverse populations are also disclosed in Gordon et al. (1994) *J. Med. Chem.* 37:1385–1401; Ecker and Crooke (1995) *Bio-*

*Technology* 13:351–360; Goodman and Ro, Peptidomimetics For Drug Design, in "Burger's Medicinal Chemistry and Drug Discovery", Vol. 1, M. E. Wolff (ed.) John Wiley & Sons 1995, pages 803–861; Blondelle et al. (1995) *Trends Anal. Chem.* 14:83–92; and Sambrook et al., *Molecular Cloning*: A Laboratory Manual, Cold Spring Harbor Press, 1989. Each of these references are herein incorporated by reference. Peptides of interest that have been identified on the basis of tissue-preferred or tissue-specific binding are described in copending applications App. Ser. No. 09/947,137, filed Sep. 5, 2001, and App. Ser. No. 09/438,150, filed Nov. 10, 1999, herein incorporated by reference. These peptides are useful in embodiments of the present invention, particularly where brain-specific or muscle-specific peptides are desired.

After in vitro screening of the peptides, the peptides of the invention are selected based on in vivo binding. Such methods for in vivo binding are known in the art. See, for example, Pasqualini et al. (1996) *Nature* 380:364–366, and the references cited therein. In some embodiments, the screening method of the peptides comprises exposing a library of molecules to the cells or tissue of interest and identifying those molecules which are capable of binding. See, for example, U.S. Pat. No. 5,622,699; U.S. Pat. No. 6,329,501, issued Dec. 11, 2001, herein incorporated by reference.

For peptides capable of binding human cells, chimpanzees can be used as the target mammal. Peptides of interest include peptides which are species-dependent and peptides which are species-independent. Thus, species-dependent peptides can be identified which do not cross react with other mammalian species; for example, a mouse-muscle-specific peptide could be identified which would decreased binding to cat muscle. Species-independent or cross-reactive peptides may also be identified. It is recognized that this may be accomplished by screening peptides in a first mammal followed by screening in at least a second mammal. One of skill will recognize that this screening protocol may be varied or expanded depending on the desired properties of the peptide, and that in vivo screening may be combined with in vitro screening in such protocols to identify peptides of interest. As noted above, because the mammal is typically sacrificed to determine binding, a primate species can be used to approximate humans, generally chimpanzees.

This in vivo selection permits determination of peptides which bind differentiated or "adult" cells and tissue types. Other methods in the art have generally selected peptides based on binding of cells in tissue culture. These are not characteristic of adult cells and tissue even if collected from developed cells and tissue, because once the cells are cultured they convert to an embryonic phenotype. (Gambke et al. (1984) *J. Biol Chem.* 259:12092–12100). One of skill in the art will recognize that peptides of interest may be selected based on a variety of properties and characteristics. Thus, peptides of interest may have different binding specificities and affinities. Thus, using the methods of the invention, cell-specific, tissue-specific, species-independent, and species-dependent peptides can be determined.

Once peptides of interest have been selected, they may be modified by methods known in the art. Such methods include random mutagenesis, as well as synthesis of the compounds for selected amino acid substitutions. Peptides of various length can be constructed and tested for the effect on binding affinity and specificity. In this manner, the binding affinity may be increased or altered. Thus, peptides may be identified which exhibit specific binding to cells of a particular tissue type, as well as peptides which exhibit specific binding and internalization by the cells of interest, e.g., muscle cells. The assays of the invention may also be used to evaluate variants of the peptide sequence(s) for enhanced affinity in a rational approach to a ligand design. The peptides find use in targeting genes, proteins, pharmaceuticals, or other compounds to particular tissue and can be used in any vector system for delivery of specific nucleotides or compositions to the target cells.

Where necessary, the nucleotide sequences encoding the peptide of interest can be used in the construction of fusion proteins or vectors for use in the invention. Such methods are known in the art. Additionally the construction of expression cassettes are known as well as promoters, terminators, enhancers, etc., necessary for expression. By nucleotide is intended gene sequences, DNA, RNA, as well as antisense nucleic acids. A number of vector systems are known for the introduction of foreign or native genes into mammalian cells. See, for example, U.S. Pat. No. 6,329,501, issued Dec. 11, 2001, and references cited therein. Standard techniques for the construction of the vectors of the present invention are well-known to those of ordinary skill in the art and can be found in such references as Sambrook et al. (1989) *Molecular Cloning: A Laboratory Manual* (2d ed., Cold Spring Harbor, N.Y.). A variety of strategies are available for ligating fragments of DNA, the choice of which depends on the nature of the termini of the DNA fragments and which choices can be readily made by those of skill in the art.

The peptides of interest can be used in any mammalian expression vector to target the expression system to the appropriate target cells. See, for example, Wu et al. (1991) *J. Biol. Chem.* 266:14338–14342; Wu and Wu (*J. Biol Chem.* (1988)) 263:14621–14624; Wu et al. (1989) *J. Biol. Chem.* 264:16985–16987; Zenke et al. (1990) *Proc. Natl. Acad. Sci. USA* 87:3655–3659; Wagner et al. (1990) *Proc. Natl. Acad. Sci. USA* 87:3410–3414.

In some embodiments, the peptides of interest are cell-binding and cell-entry peptides. Generally, the peptides of interest will comprise at least about 5 to about 50 amino acids, preferably at least about 5 to about 30 amino acids, more preferably at least about 7 to about 20 amino acids. It is recognized that consensus sequences may be identified among the peptides that are capable of binding to a ligand. Such consensus sequences identify key amino acids or patterns of amino acids that are essential for binding. Consensus sequences may be determined by an analysis of peptide patterns that are capable of binding particular cells or tissue. Once recognized, the consensus regions may be used in constructing other peptides for use in targeting particular cells or tissue. Consensus sequences may be tested by constructing or synthesizing peptides and determining the effect of the consensus sequence on binding. In this manner, as long as the consensus sequence is present, the peptide will bind the ligand. In some cases, longer peptides will be useful, as they may be more easily bound or more readily enter into the target cell.

The peptides can be classified into linear, cyclic and conformational types. While the invention is not bound by any particular mode of action, it is postulated that the shorter peptides, generally from about 7 to about 20 amino acids, are involved in linear binding to the selected cells, while longer peptides assume conformational folding and are involved in conformational binding. Cyclic peptide structures can also be constructed. In this manner, a core peptide region such as a consensus peptide binding sequence will be flanked with cysteine amino acids to form cyclic peptides. Such libraries are available commercially, for example the Ph.D. phage display peptide library kits from New England Biolabs, Inc. See also, Parmley et al. (1988) *Gene* 73:305–318; Cortese et al. (1995) *Curr. Opin. Biotechnol* 6:73–80; Noren (1996) *NEB Transcript* 8(1):1–5; and Devlin et al. (1990) *Science* 249:404–406.

In this manner, peptide-directed therapies are useful for the treatment of a number of acquired and inherited diseases. Previous gene transfer approaches have been limited by relatively low efficiencies of gene transduction. Thus, the present approach provides a means to increase recombinant gene expression and pharmaceutical concentration in the cells and/or tissues of interest.

The peptide of interest is coupled to a sensor to create the LSD of the invention. When coupled to the sensor, the peptide of interest is capable of interacting with ligands and this interaction is detected by the sensor. In some embodiments, the peptide of interest is biotinylated and coupled to a sensor prepared with a Langmuir-Blodgett film of biotinylated phospholipid. In such embodiments, the assembly of the LSD may be accomplished by the addition of streptavidin to couple the peptide of interest to the sensor. One of skill in the art is aware that the order of the steps of the assay method may be varied where practical or where the order is immaterial; for example, the peptide of interest may be prepared to be coupled to the sensor after the sensor is prepared to be coupled to the peptide of interest.

The coupling composition layer of the LSD is the layer which couples the peptide of interest to the sensor. In some embodiments, this coupling composition layer is composed of streptavidin and biotin. Any composition or coupling method may be used so long as the peptide of interest is coupled to the sensor and the LSD is capable of detecting the binding of a ligand to the peptide of interest. Thus, in some embodiments, a sensor is coated with gold or a gold-coated sensor is obtained; the sensor is then coated with streptavidin and coupled to the biotinylated peptide of interest. Alternatively, the coupling composition layer may comprise a biotinylated thiol or disulfide layer which is linked directly to a layer of gold; the biotinylated layer is then linked to streptavidin and the biotinylated peptide of interest. See, for example, Luppa et al. (2001) *Clinica Chimica Acta* 314: 1–26; Gau et al. (2001) *Biosensors & Bioelectronics* 16: 745–755.

The peptide of interest may optionally be combined with a spacer to enhance the performance of the LSD. Spacers may be short peptides which are synthesized in continuous linkage with the peptide of interest to create a combination of the peptide of interest and the spacer; this combination may then be biotinylated or chemically modified in order to couple it to the sensor. One of skill will recognize that the length of the spacer may affect the efficacy of the LSD: if the spacer is too short, the ligand will not have sufficient access to the peptide and binding will be decreased; if the spacer is too long, the orientation of the peptide may be disadvantageously altered. A peptide spacer may be 1, 2, 3, 4, 5, 6, 7, 8, 9, 10, 11, 12, 15, 20, 25, 30, or more amino acids in length. One of skill can adjust the length of the spacer to optimize the efficacy and sensitivity of the LSD.

The LSD includes a piezoelectric crystal sensor. In some embodiments, an acoustic wave sensor is used which comprises an AT-cut planar quartz crystal with a 5 MHz nominal oscillating frequency. Such crystals, suitable for acoustic wave devices (AWD), are commercially available (e.g., Maxtek, Inc). The crystals or sensors may be supplied with electrodes, for example, crystals may be supplied with circular gold electrodes deposited on both sides of the crystal for the electrical connection to the oscillatory circuit.

In some embodiments, a mass-sensitive sensor is used; alternatively, other sensors may be used so long as they are capable of detecting the binding of peptide of interest to ligand and providing signal output that changes in response to that binding. A direct correlation of binding and signal output is not required so long as the desired result is obtained. Thus, when binding occurs, different physical and electrochemical properties of the sensor may be changed: mass; free energy; electrical properties such as charge and conductance; optical properties such as fluorescence, luminescence, adsorption, scatter, and refraction. Accordingly, suitable sensors include electrochemical, calorimetric, and optical sensors. See, for example, Luppa et al. (2001) *Clinica Chimica Acta* 314: 1–26. One of skill in the art will appreciate that for different applications of the assays of the invention, sensors with different sensitivities and outputs may be used. Thus, for example, in some applications a preferred LSD will be capable of high-resolution quantitation of changes in binding, while for other applications an LSD need only detect the presence or absence of high-affinity binding.

In some embodiments, a Maxtek 740 sensor is used which has a working frequency of 5 MHz. One of skill recognizes that the working frequency corresponding to the highest sensitivity of the LSD system can be identified to optimize the changes in the resonance frequency of the sensor when ligand is bound. Any suitable device may be used to monitor the signal output from the sensor, for example, an HP4195A Network/Spectrum Analyzer (Hewlett-Packard) can be used. The analyzer device scans a set range of frequencies and measures the signal properties at each frequency. After the optimal frequency is found for a particular peptide/ligand combination this frequency can be used as a working frequency for sensitive measurements of binding; useful frequencies are generally between 2 MHz and 150 MHz.

The sensor is prepared to be coupled to the peptide by any suitable method. For example, a Langmuir-Blodgett film of biotinylated lipid is added to the sensor. Langmuir-Blodgett films are formed from at least one monolayer. A monolayer is a one molecule thick film of at least one amphiphilic compound or composition that forms at the air/water interface of an aqueous solution. Each molecule in the monolayer is aligned in the same orientation, with the hydrophobic domain facing the air and the hydrophilic domain facing the aqueous solution. Compression of the monolayer results in the formation of an ordered two dimensional solid that may be transferred to a substrate by passing the substrate through the monolayer at the air/water interface. A monolayer that has been transferred to a substrate is termed a Langmuir-Blodgett film, or LB film. For reviews of Langmuir-Blodgett technology, see Gaines, G. L. Jr. (1966) *Insoluble Monolayers at Liquid-Gas Interfaces*, Interscience, New York; Zasadzinski et al. (1994) *Science* 263:1726–1733; Ullman (1991) *An Introduction to Ultrathin Organic Films*, Academic Press, Boston, Mass.; and Roberts (1990) *Langmuir-Blodgett Films*, Plenum, New York; the contents of which are incorporated herein by reference.

Monolayers are typically composed of organic molecules such as lipids, fatty acids and fatty acid derivatives, fat soluble vitamins, cholesterol, chlorophyll, valinomycin and synthetic polymers such as polyvinyl acetate and polymethyl methacrylate. Monolayers may also be formed by many other amphiphilic compounds; thus, many amphiphilic compounds may be used to form the monolayers of the invention. Such compounds include lipids having at least 14 carbon atoms. Examples include stearic acid and hexadecanoic acid. Other compounds that will form monolayers include, but are not limited to those described in Gaines, G. L. Jr. (1966) *Insoluble Monolayers Liquid-Gas Interface*, Interscience, New York, the contents of which are incorporated by reference.

Lipid monolayer depositions may be carried out by methods known in the art and as described in copending application Ser. No. 09/452,968, filed Dec. 2, 1999, herein incorporated by reference in its entirety. Langmuir-Blodgett (LB) film balances are commercially available, for example from KSV-Chemicals, Finland, and are operated in accordance with the supplier's instructions.

The Langmuir-Blodgett film is formed by the successive transfer of monolayers onto the surface of the sensor using the Langmuir-Blodgett technique. In some embodiments, biotinylated lipid solutions are spread on the aqueous subphase as hexane solutions. The monolayer is then compressed and a vertical film deposition is performed. In LB film deposition, multiple monolayers may be added to the sensor by successive dipping of the sensors through the monomolecular film deposited at the air/liquid interface. LB films may be formed by the addition of one, two three, four, five, six, seven, eight, nine, ten, eleven, twelve, thirteen, fourteen, fifteen or more monolayers in this manner to create the final Langmuir-Blodgett film.

The monolayers used to create the Langmuir-Blodgett film may be formed without the aid of a volatile organic solvent. See, for example, copending application Ser. No. 09/452,968, filed Dec. 2, 1999, hereby incorporated by reference in its entirety. Many methods for forming LB films require dissolution of the compounds to be formed into a monolayer in a volatile organic solvent such as hexane. The organic solvent forms a separate phase from the aqueous solution and functions to prevent dissolution of the monolayer components in the aqueous phase. After spreading the mixture at the air-liquid interface of the aqueous solution, the solvent is allowed to evaporate, leaving a monolayer at the interface. However, the organic solvent may damage the monolayer components and leave an undesirable residue. LB films formed from such monolayers may have unacceptable levels of nonspecific, non-saturable binding which hampers quantitative measurement of specific binding. Thus, in some embodiments, monolayers formed without the aid of an organic solvent as set forth in copending application Ser. No. 09/452,968, filed Dec. 2, 1999, provide improved properties to the LSDs of the present invention. In some embodiments, a peptide of interest is covalently bound or linked to phospholipids; vesicles comprising these phospholipids are then used to create monolayers and LB films to make an LSD of the invention. In such embodiments, the coupling of the peptide of interest to the sensor may be accomplished by the formation of such an LB film on the sensors and does not necessarily require a coupling via streptavidin and biotin interactions. Such sensors may be gold-plated or coated with other material to facilitate the adherence of the LB film to the sensor.

Generally, the formation of a monolayer without the aid of an organic solvent is formed by layering an amphiphilic compound or composition onto an aqueous subphase by slowly allowing this compound or composition to run down an inclined wettable planar surface that is partially submersed into the subphase. The formation of a monolayer in this way comprises the steps of:

(a) providing a composition comprising at least one amphiphilic compound, wherein said composition contains not more than 25% of a volatile organic solvent and may optionally contain one or more compounds of interest;

(b) immersing one end of a wettable planar surface into an aqueous subphase, wherein said planar surface forms an angle of about 90–170 degrees to an upper surface of said subphase, wherein said subphase comprises at least one monovalent cation and at least one bivalent cation, wherein said subphase has a pH of 4.0–8.0;

(c) delivering said composition at a rate of about 0.02–4.0 ml per minute to said planar surface to form a monolayer; and (d) compressing said monolayer.

"Aqueous" as used herein refers to a solution in which water is the solvent. "Cation" as used herein refers to any positively charged atom. Examples of bivalent cations useful in the subphase solution include, but are not limited to calcium, cadmium and magnesium. Examples of monovalent cations useful in the subphase solution include, but are not limited to sodium and potassium. "Amphiphilic compound" as used herein refers to a molecule that is insoluble in water and has a hydrophilic region that will preferentially face an aqueous phase and a hydrophobic region that will preferentially face the air or a nonaqueous phase. As used herein, "amphiphilic compound" also refers to molecules that may be soluble in an aqueous solution at low concentration, but will form micelles or liposomes or vesicles above a critical concentration. In some embodiments of the invention, a monolayer is formed from vesicles of biotinylated phospholipid.

"Compressing" as used herein refers to moving one or more compression barriers of a Langmuir-Blodgett apparatus so as to reduce the surface area in which the monolayer has formed. As this surface area decreases, the intermolecular distance decreases and the surface pressure increases. This relationship may be graphically represented by an isotherm, which plots the surface pressure versus the area per molecule. "Delivering" as used herein, refers to any method used to apply the composition to be formed into a monolayer onto the planar surface. Preferably, the composition is delivered to the planar surface using a micropipette. However, those skilled in the art will know of variety of delivery options that may be used in the methods of the invention. The rate of delivery of the composition to the planar surface will be about 0.02–4.0 ml per minute, preferably about 0.05–0.75 ml per minute, and most preferably about 0.1 ml per minute. "LB Film" as used herein refers to a monolayer that resides on the surface of a substrate, such as a piezoelectric crystal sensor.

"Monolayer" as used herein, refers to a one molecule thick film of at least one amphiphilic compound or composition. "Piezoelectric" as used herein, refers to the ability to generate a voltage when mechanical force is applied, or to generate a mechanical force when voltage is supplied. This reciprocal relationship is referred to as the piezoelectric effect. The absence of a center of symmetry in the piezoelectric crystal is necessary for the piezoelectric effect. Of the 21 classes of crystals that lack a center of symmetry, all but one class are piezoelectric. A preferred piezoelectric crystal is a quartz crystal.

"Subphase" as used herein refers to an aqueous solution onto which the composition to be formed into a monolayer is spread. At least one bivalent and one monovalent cation must be present in the subphase. Suitable subphase include but are not limited to those described by Gains ("Insoluble monolayers at liquid-gas interface." (1996) Interscience, New York). A typical subphase comprises: 55.0 mM KCl, 4.0 mM NaCl, 1.0 mM $MgCl_2$, 0.1 mM $CaCl_2$ and 2.0 mM MOPS buffer in deionized doubly distilled water, pH 7.4. The subphase is placed in the trough of the Langmuir-Blodgett apparatus prior to spreading the monolayer. "Volatile organic solvent" as used herein refers to an organic liquid that is nonmiscible with water, has a density less than 1.0, a boiling point of less than 100° C. and is capable of dissolving an amphiphilic compound. Examples of volatile organic solvents include chloroform, hexane, benzene, decane and ether.

One skilled in the art of monolayer formation will be able to empirically determine the angle and delivery rate best suited to a particular application. The following criteria should be applied to assess the efficiency of the spreading procedure:

1. The loss of the spreading material should be minimized. The loss can be estimated by the recovery coefficient defined as $R=M_m/M_s$, where $M_s$ is the mass of the substance in the spreading solution, and $M_m$ is the mass of the monolayer. In the successful spreading procedure the R should be close to 1.0. An R<1 indicates losses of the substance. For example, R=0.5 would indicate 50% loss of the spreading material.

2. The spreading procedure should not cause significant changes in physical chemical activity of the spread substance. For example, at the very low rate (<0.01 ml/min) and in the absence of lipids, proteins may produce monolayers with unfolded and denatured molecules.

Compression of a monolayer results in a transition from a gas phase to a liquid phase. Additional compression results in a transition from a liquid phase to a solid phase in which the molecules of the monolayer form a tightly packed, ordered structure. Further compression results in a collapse of the monolayer due to mechanical instability and a concomitant decrease in surface pressure. If the monolayer has more than one component, for example an antibody component, there may be a first collapse pressure at which the antibodies collapse and a second higher collapse pressure at which the rest of the monolayer collapses. Graphing of the surface pressure in response to movement of the compression barrier produces an isotherm that may be used to determine the optimal compression for a particular monolayer under a particular set of conditions. The optimal surface pressure is achieved just before a pressure is reached that results in the collapse of one or more monolayer components.

After the desired surface pressure is achieved by compression of the monolayer, an LB film may be formed by passing a substrate through the monolayer one or more times. Methods of forming LB films are known to those skilled in the art and are described in Ullman (1991) *An Introduction to Ultrathin Organic Films*, Academic Press, Boston, Mass.; and Roberts (1990) *Langmuir-Blodgett Films*, Plenum, New York; the contents of which are incorporated herein by reference.

Once the LSD is prepared, the signal output may be measured by any suitable device which is compatible with the crystal or sensor used to create the LSD. Many such devices are known in the art and are commercially available. In some embodiments, measurements are carried out using a PM-740 Maxtek plating monitor with a frequency resolution of 0.5 Hz at 5 MGz. By "signal output" is intended any property of the sensor that changes in response to binding of a ligand and can be detected or monitored by a suitable device. Signal output of the device may be recorded and analyzed using a personal computer and appropriate data acquisition card and software. In some embodiments, the resonance frequency varies with the mass of the crystal as it changes due to interaction of ligands with the sensor. Because the voltage output from the Maxtek device is directly related to the resonance frequency of the quartz crystal sensor, changes in the resonance frequency and/or voltage may then be used to monitor the binding of ligand to the peptide of interest. The change in frequency and voltage will be proportional to the concentration of ligand, provided that nonspecific binding is low. Once prepared, an LSD may be used for multiple assays and may remain functional for a long period of time, up to a day, several days, a week, or a month or more.

In methods and compositions for performing binding assays, it is desirable to have: (1) high surface density of peptides of interest; (2) high specificity of peptide-ligand interactions and a low level of non-specific binding; (3) accessibility of interacting peptides of interest; and (4) stability of the sensing system. LSDs of the invention show improved properties over previously known devices, including superior response time and faster achievement of a steady-state signal output. (Pathirana et al. (2000) *Biosensors & Bioelectronics* 15: 135–141).

The present invention overcomes these problems by providing methods for forming LSDs with improved sensitivity and response times. As a result, binding assays may be rapidly performed and quantitated.

The LSD is exposed to one or more ligands, typically by layering a solution of homogenate of the tissue or cell type of interest onto the LSD, although cell suspensions or other types of cell or tissue preparations may also be used. In other embodiments, solutions of purified or somewhat purified ligands may be exposed to the LSD. Thus, any tissue sample may be assayed for the presence of ligands by exposure to an LSD, so long as the form of the sample is compatible with exposure to the LSD. By "tissue sample" as used herein is intended a cell or tissue homogenate, a cell culture or cell suspension, an extract of cellular or tissue material, or a purified or partially purified ligand solution. By purified or partially purified ligand solution is intended that the ligand used to make the solution is substantially free of cellular material and includes preparations of ligand having less than about 30%, 20%, 10%, 5%, 4%, 3%, 2%, or 1% (by weight) of contaminating material. It is recognized that a ligand may represent any component of the tissue or cell type of interest present in a tissue sample that binds to or interacts in a detectable way with the peptide of interest. Thus, a ligand may represent a proteinaceous component of the tissue or cell type or it may represent some other cellular component. Thus, for example, a ligand may be a cell recognition molecule, for example, a receptor, as well as a cell-surface molecule or cell-surface molecular marker.

In addition to providing assays for identifying ligands of peptides of interest, one of skill will recognize that the present invention has many applications. For example, the present invention provides assays and compositions for identifying solutions and compositions that do not interact with a peptide of interest. Thus, the present invention provides both positive and negative assays as well as quantitative binding assays which may be used in a variety of applications, for example, to design peptides or peptide moieties which may have particular properties. In this manner, ligands may also be compounds or compositions that may be useful because of their interaction or lack of interaction with the peptide of interest. For example, a ligand may be a pharmaceutical compound which binds to the peptide of interest. Such compounds or chemicals may be used to block undesired localization of other compounds or chemicals and thus reduce the non-specificity and side-effects of a treatment. Thus, in a manner similar to the blocking experiment described herein and shown in FIG. 3, either the peptides of interest or their ligand(s) could be used as blocking agents to increase the specificity of other treatments. The present invention provides assays and compositions for identifying and characterizing such blocking ligands.

It is understood that the tissue sample to which the LSD is exposed may come from one or several species and thus more than one ligand, or multiple ligands with different characteristics, may be present in and identified from a tissue sample. Tissue samples may come from species used in the in vivo screening used to identify the protein of interest or it may come from different species. One of skill in the art will recognize that the tissues and species used in the in vivo screening and selected for the tissue sample will vary depending on the desired characteristics of the ligand or the property of the ligand which is being evaluated. Tissue samples, including homogenates, may come from whole animals or tissue or tissue culture from any species. For example, tissue samples may be prepared from human tissue or primary human cell cultures, or from other human cell cultures.

Construction of lipid vesicles. Large, unilamellar liposomes may be prepared from suitable compounds, for example, synthetic L-α-(1,2-dipalmitoyl-sn-glycero-3-phosphocholine) (DPPC) and maleimido phenyl butyrate phosphatidylethanolamine (MPB-PE). In some embodiments, peptides of interest are covalently linked to phospholipids, which are used to prepare liposomes. Liposomes are converted into monolayers and deposited on the sensor surface by the Langmuir-Blodgett method.

Monolayer techniques. Surface Film Balance. Measurements of surface pressure are performed on a Langmuir-Blodgett film balance KSV 2200 LB (KSV-Chemicals, Finland). The fully computerized system contains a Wilhelmy-type surface balance (range 0–100 mN/m; sensitivity 0.05 mN/m), a Teflon trough (45×15 $cm^2$), a variable speed motor-driven Teflon barrier (0–200 mm/min), and a laminar flow hood. The trough is mounted on a 200 kg marble table. Vibration control is provided by interposing rubber shock absorbers, and by mounting the laminar flow hood on a separate bench. Surface pressure is monitored by use of a sandblasted platinum plate of 4 cm perimeter.

Temperature of the subphase is controlled (±0.1° C.) by water circulation through a quartz tube coil on the bottom of the trough. Temperature is measured by a thermistor located just below the water interface. Surface pressure data are collected during slow, steady-state compression of the monolayers.

Free energy, enthalpy and entropy. The thermodynamic value of free energy, enthalpy, and entropy derived from the isothermal compression data are calculated by using the following equations (Ito et al. (1989) *Thin Solid Films* 180:1–13; Vodyanoy et al. (1990) *Biochim Biophys Acta* 1047:284–289; Vodyanoy et al. (1994) *Langmuir* 10:1354–1357; Pathirana et al. (1992) *J. Am. Chem. Soc.* 114:1404–1405, Pathirana et al. (1992a) *Langmuir* 8:1984–198, Pathirana et al. (1996) *Supramolecular Science* 3:149–154, Pathirana et al.(1998) *Langmuir* 14:679–682.

$$(\Delta G) = \int_{P=0}^{P=x} A dP$$

$$\Delta H = \Delta G + T\Delta S$$

$$(\Delta S)_P = -[\partial(\Delta G)/\partial T] + (\partial c_w/\partial T)_P (A_{P=0} - A_{P=x})$$

$$c_w = 75.680 - 0.138t - 3.56*10^{-4}t^2 + 4.7*10^{-7}t^3,$$

where ΔG, ΔH and ΔS are free energy, enthalpy and entropy of compression; $c_w$, is the surface tension of pure water, A and P are surface area and pressure, and T is the absolute temperature and t is the temperature (ΔC).

Surface potential. Surface potentials are measured with a $^{210}$Po air electrode located 2 mm from the water surface connected to an electrometer, and referenced to an Ag—AgCl electrode immersed in the subphase. Surface potential V and area A isotherms are measured simultaneously with the surface pressure isotherms and are used for calculations of the surface dipole moments μ from the equation μ=AV/12π, where A(Å$^2$/molecule) is the molecular area, V is in millivolts, and μ is in millidebye units (Gaines, G. L. Jr. (1996) *Insoluble Monolayers at Liquid-Gas Interface*, Interscience, New York and Pathirana et al. (1992) *J. Am. Chem. Soc.* 114:1404–1405).

Elasticity. The monolayer elasticity E=−A(∂P/∂A)$_T$ as a function of the surface pressure, is calculated directly from the pressure isotherms (Vodyanoy et al. (1990) *Biochim Biophys Acta* 1047:284–289).

Viscosity. The surface viscosity of the monolayers is measured by the canal viscometer by replacing the solid compression barrier of the LB trough with the one containing a 0.265×2.0 $cm^2$ slit. The monolayer is allowed to flow through a slit in the water surface, from a region of surface pressure, $P_2$, to one where the surface pressure has a lower value, $P_1$. Jody's formula (Gaines, 1966) is used for calculation of the surface viscosity, $(\eta_S,)$:

$$Q=(P_2-P_1)/(cl\eta_0)[a-2(\eta_s/c\eta_0)^{1/2} \tan h(c\eta_0/\eta_s)_{1/2}a/2]$$

where a and l are the width and length of the canal, Q is the area of monolayer flowing through the canal per second, $\eta_0$ is the bulk viscosity of the subphase liquid, and $c\eta_0$=0.191 is a device constant.

The following examples are intended to illustrate, rather than to limit the invention.

Experimental

In this working example, a peptide selected in vivo for murine myofibers using a 7-mer phage display peptide library and having the sequence ASSLNIA (SEQ ID NO:1) was immobilized onto the surface of an acoustic wave sensor by biotin-streptavidin coupling. The sensor was exposed to samples of tissue homogenates, and binding of ligands was recorded. The sensor showed a strong response to murine muscle homogenates. The interaction was specific since preincubation of the muscle homogenates with free peptide resulted in significantly reduced signal. Feline muscle homogenates caused appreciable, but lower responses compared to those from murine muscle, indicating that the peptide was able to bind its putative receptor across species boundaries. In contrast, murine kidney, liver, and brain preparations produced insignificant responses, thus demonstrating the capability of the LSD of the invention to determine the potential relevance of a ligand for a variety of species.

EXAMPLE 1

Preparation of a Ligand Sensor Device and Assay

In this example, a peptide of interest was identified and used to prepare a ligand sensor device to evaluate ligands of the peptide of interest. Specifically, a peptide selected in vivo for binding to murine myofibers and having the sequence ASSLNIA was coupled to a sensor by biotin-streptavidin coupling; the resulting ligand sensor device was used to perform assays on mouse and cat muscle tissue homogenates.

Identification of a peptide of interest. Mice were euthanized with carbon dioxide gas and cats were euthanized with an overdose of pentobarbital administered intravenously (the use of animals was approved by the Auburn University Animal Care and Use Committee). After death, animals were perfused with ice-cold Phosphate Buffered Saline (PBS). Samples of mouse and cat skeletal muscle, mouse kidney, liver and brain were harvested. Tissue aliquots (200 mg) were homogenized in 4 ml PBS using a manual homogenizer. Immediately after homogenization samples were microcentrifuged for 10 min at 3,000 rpm, and the supernatants containing tissue vesicles were separated from the pellets. Tissue homogenization resulted in the formation of vesicles, "mini-cells" whose membranes are identical to the cell membrane. Vesicle concentration and integrity were examined by dark-field microscopy (Vodyanoy et al. (1994) *Langmuir* 10: 1354–1357). Dilutions of tissue samples were prepared in PBS as follows: 1:5, 1:25, 1:125, and 1:625. To perform the blocking experiment, free ASSLNIA peptide (1 mg/ml) synthesized by Research Genetics, Inc. (Huntsville, Ala., USA) was added to the murine skeletal muscle tissue homogenate (50 mg/ml) and incubated at room temperature for 1 hour with agitation. Protein concentration in tissue samples was determined using Bio-Rad® Protein Assay Kit (Bio-Rad Laboratories, Hercules, Calif., USA).

A 7-mer phage display peptide library (New England Biolabs, Inc., Beverly, Mass., USA) was screened as described in Samoylova and Smith (1999) *Muscle & Nerve* 22: 460–466. A peptide of interest specific to murine skeletal muscle was identified. This peptide was found to bind myofibers of murine skeletal muscles. The sequence of this peptide was determined by conventional techniques to be: ASSLNIA (SEQ ID NO:1). The peptide was synthesized in combination with a spacer (GGGSK; SEQ ID NO:2) added to the C terminus and modified by coupling to biotin, and the biotinylated peptide was then HPLC purified to 98% by Peptide Technologies Corporation (Gaithersburg, Md., USA) and used to prepare a ligand sensor device.

Preparation of the sensor. AT-cut planar quartz crystal sensors with a 5 MHz nominal oscillating frequency were purchased from Maxtek, Inc. Circular gold electrodes were deposited on both sides of the crystal sensor for the electrical connection to the oscillatory circuit. The sensor was prepared to be coupled to the peptide by the addition of a Langmuir-Blodgett film of biotinylated lipid. Lipid monolayer depositions were carried out using a Langmuir-Blodgett (LB) film balance KSV 2200 LB (KSV-Chemicals, Finland). This fully computerized system includes a Wilhelmy-type surface balance (range 0–100 mN/m; sensitivity 0.05 mN/m), a Teflon trough (45×15 cm$^2$), a variable speed motor-driven Teflon barrier (0–200 mm/min), and a laminar flow hood. The trough was mounted on a 200 kg marble table. Vibration control was provided by interposing rubber shock absorbers and by mounting the laminar flow hood on a separate bench. Surface pressure was monitored by use of a sandblasted platinum plate of 4-cm perimeter. The temperature of the aqueous subphase (20° C. ±0.1° C.) was controlled by water circulation through a quartz tube coil on the bottom of the trough. The temperature of the aqueous subphase was measured by a thermistor located just below the air/liquid interface.

Monolayers were transferred onto the gold surface of an acoustic wave sensor using the Langmuir-Blodgett technique. Lipid solutions were spread on the aqueous subphase as hexane solutions (1 mg/ml) containing 2% ethanol (Ito et al. (1989) *Thin Solid Films* 180: 1–13). The lipid solutions contained phospholipid (N (biotinoyl)-1,2-dihexadecanoyl-SN-glycero-3-phosphoethanolamine). The aqueous subphase was a solution containing 55 mM KCl, 4 mM NaCl, 0.1 mM CaCl$_2$, 1 mM MgCl$_2$ and 2 mM 3-(N-morpholino)-propanesulfonic acid (MOPS) made with deionized double distilled water (pH 7.4). After spreading, the monolayer was allowed to equilibrate and stabilize for 10 min at 19° C. The monolayer was then compressed at a rate of 30 mm/min and a vertical film deposition was carried out with a vertical rate of 4.5 mm/min and at a constant surface pressure of 25 mN/m. Multiple monolayers were added by successive dipping of the sensors through the monomolecular film deposited at the air/liquid interface. Eleven monolayers were transferred to the gold surface of the quartz crystals in this manner to create the final Langniuir-Blodgett film.

Coupling the peptide of interest to the sensor. The sensor, prepared as described above by the addition of a Langmuir-Blodgett film of biotinylated lipid, was then coupled to the peptide of interest by molecular assembly with streptavidin. Streptavidin was diluted to a final concentration of 0.01 mg/ml in the subphase solution and exposed to the LB film for 2 hours; the film was then rinsed with distilled water and dried for 2 min in ambient air. The LB film was then treated with a solution of the biotinylated peptide of interest (ASSLNIAGGGSK (SEQ ID NO:3)-Biotin at 0.001 mg/ml in subphase solution) for 2 hours, rinsed and dried again as above. If necessary, this preparation step could be followed by a blocking step with a biotin solution. In this manner, the peptide of interest was coupled with the phospholipid via molecular assembly with streptavidin (see FIG. 1), thereby coupling the peptide of interest to the sensor to create the ligand sensor device (LSD). Each LSD was placed in an individual Petri dish and stored no longer than 24 hours at 4° C. until affinity assays were performed.

Quantifying the signal output from the ligand sensor device (LSD). Measurements were carried out using a PM-740 Maxtek plating monitor with a frequency resolution of 0.5 Hz at 5 MHz. The voltage output from the Maxtek device is directly related to the resonance frequency of the quartz crystal sensor. Changes in the resonance frequency of the quartz crystal sensor were used to monitor the binding of homogenate vesicles to the sensor surface. The observed changes are hypothesized to be due both to viscoelastic changes of the LB film-vesicles near surface fluid media and the mass change associated with binding of the vesicles.

To evaluate the affinity of a ligand, the LSD was positioned in the probe arm of the instrument just before delivery of samples. Immediately after recording was started, 1000 µl phosphate buffered saline (PBS) was delivered with a pipette to the dry sensor surface and voltage was recorded for 4–8 minutes. The PBS was then removed carefully with a plastic pipette tip and a new recording was initiated. Tissue homogenates of different dilutions were added sequentially to the sensor and the same measuring procedure was followed after each addition. Each experiment was replicated 2–4 times, and the temperature of all samples was 25° C. Voltage output of the LSD was recorded and records were analyzed offline.

Analysis of LSD output. The ratio of occupied (Y) and free (1−Y) peptide molecules on the sensor surface can be defined as $$Y/(1-Y)=K_b[C]^n \quad (1)$$

where $K_b$ is the association binding constant, C is a protein concentration in the tissue sample, and n is the number of molecules bound to a single peptide (Pathirana et al. (2000) *Biosensors & Bioelectronics* 15: 135–141). Taking the logarithm of both sides the following is derived:

$$\log(Y/(1-Y))=\log K_b+n\log[C] \quad (2).$$

A plot of the left-hand side of equation (2) versus log[C] is known as a Hill plot. (Kuchel and Ralston (1988) *Theory* and *Problems of Biochemistry* (McGraw-Hill, New York). It gives an estimate of n from the slope, $K_b$ from the ordinate intercept, and $EC_{50}$ at the point when $Y=1-Y$.

Figure 2:
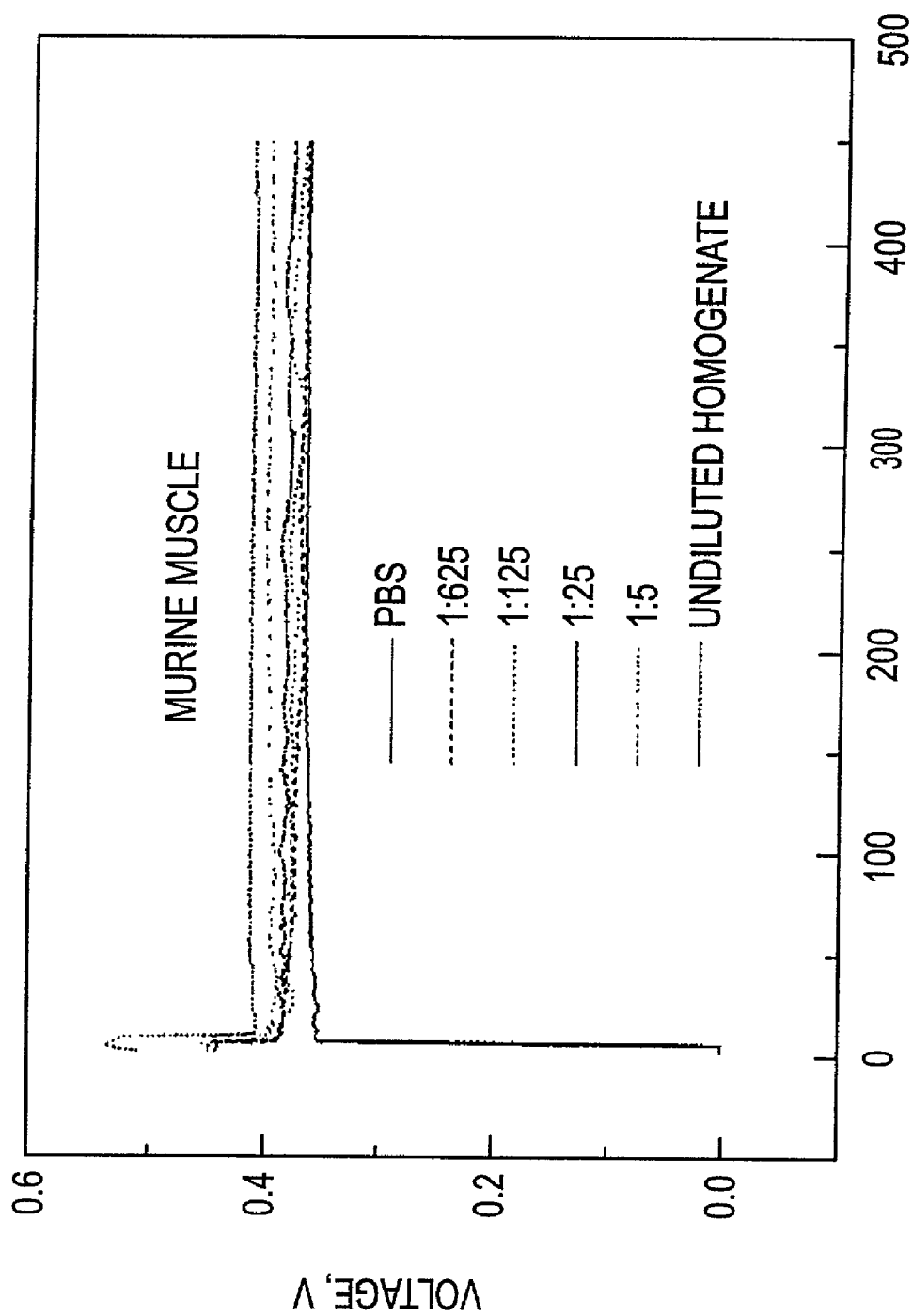
FIG. 2 shows results of an experiment with an exemplary ligand sensor device (LSD). The graph shows typical LSD signal output. In the example shown, the LSD was prepared using the exemplary peptide of interest having the amino acid sequence ASSLNIA (SEQ ID NO:1). The reference or baseline signal output measurement was made after exposure of the LSD to phosphate buffered saline (PBS) with no homogenate. The ligand sensor device was exposed to murine muscle homogenate at various levels of dilution, including undiluted (3.8 mg/ml of protein), 1:5, 1:25, 1:125, and 1:625. Each line in the graph represents approximately 480 data points taken once a second during 8 minutes of quantifying the signal output from the ligand sensor device.

FIG. 2 shows the ligand sensor device (LSD) signal output dose-response curves obtained with varying dilutions of murine skeletal muscle homogenate. LSDs were exposed to sequential applications of homogenates beginning with the most dilute solution and ending with the undiluted homogenate. LSDs under these circumstances showed elevations of voltage with each application, indicating that additional material was binding to the film with each increase in homogenate concentration. It was observed that the initial delay in signal output response ($\tau_1=8\pm1$ sec) does not depend on the homogenate concentration. Rather, for each homogenate concentration, the sensor signal output approaches a steady-state value corresponding to that concentration within 100 sec ($\tau_2=70\pm20$ sec).

As shown in FIG. 2, the LSD response is distinguished by fast reaction time, the attainment of a steady state, and low non-specific binding. While the invention is not bound by any theory of operation, these properties may be attributable to the placement of the peptide molecules in an environment that allows rapid binding due to the favorable orientation of the peptide and distance from the sensor.

Figure 3:
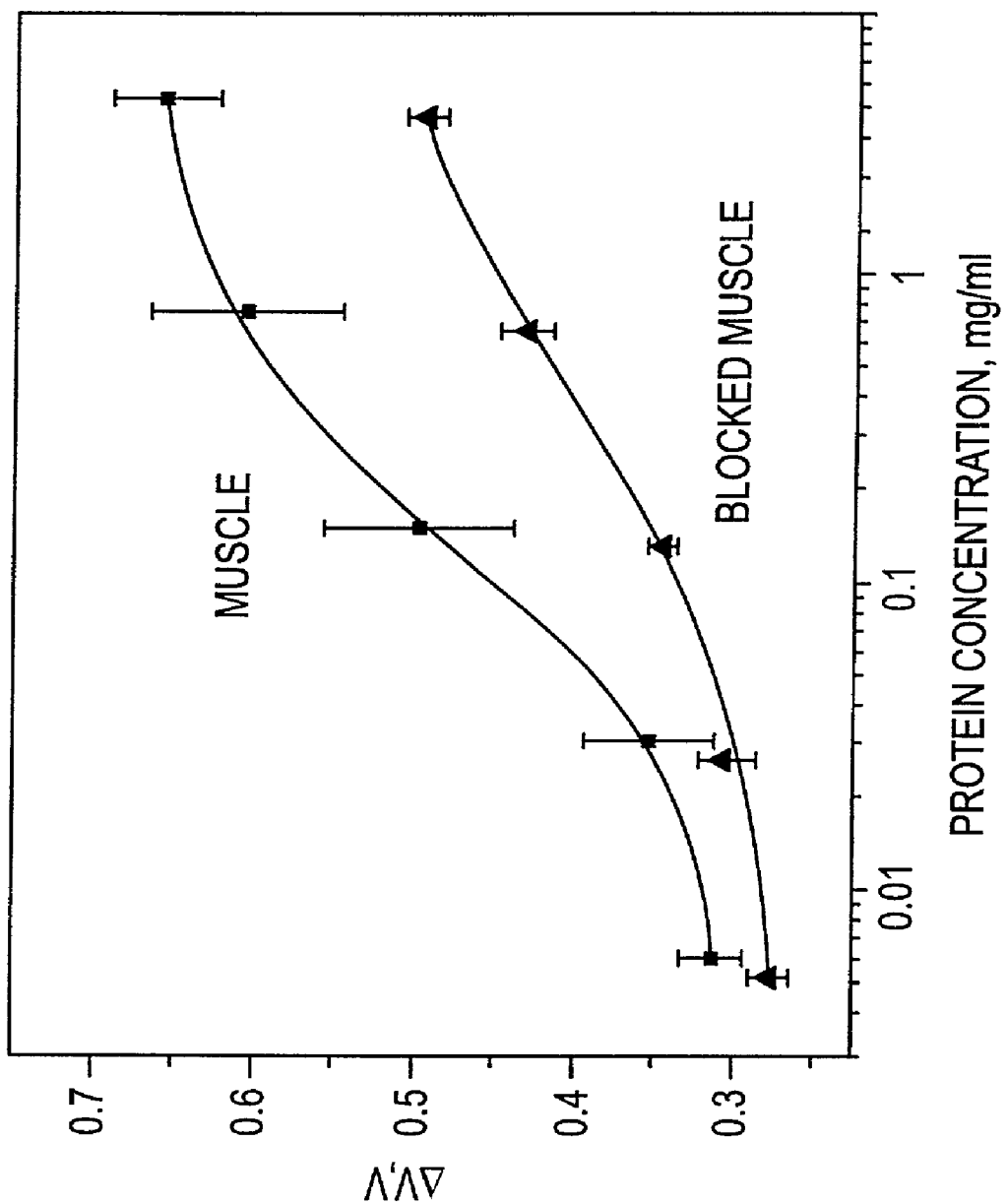
FIG. 3 shows dose-response curves of exemplary signal output from a ligand sensor device as a function of protein concentration. The upper dose-response curve ("Muscle") represents the mean values of steady-state signal output as a function of protein concentrations from $6.0 \times 10^{-3}$ to 3.8 mg/ml in murine muscle homogenates. The lower curve ("Blocked muscle") shows the sensor dose-responses to muscle homogenates where the sensor was preincubated ("blocked") with free peptide of interest (here, a 1 mg/ml solution of the ASSLNIA peptide). Signal output values were obtained by averaging about 200 data points of each steady-state level of response curve (as shown in FIG. 2); bars represent standard deviation. Smooth curves are the sigmoid fits to the experimental data ($\chi^2$=0.199, $R^2$=0.999, muscle; $\chi^2$=0.053, $R^2$=0.999, blocked muscle). Changes in signal output ($\Delta V$) were calculated by subtraction of the mean value of the signal output from a sensor exposed to PBS from the mean value of the signal output from a sensor exposed to muscle homogenate solutions.

Results demonstrating binding specificity and cross-species affinity. In FIG. 3, the upper curve ("Muscle") shows the mean values of the steady state LSD signal output plotted as a function of the relative concentration of the murine muscle homogenates. This binding dose-response curve had a typical sigmoid shape and the signal was saturated at a protein concentration of about 5.0 mg/ml. The lower curve of FIG. 3 ("Blocked muscle") illustrates the specificity of the interaction of the muscle homogenate with the peptide of interest. The lower curve shows that preincubation of the murine muscle homogenate with free peptide significantly reduced the LSD signal output.

A Hill plot equation (see equation 2 above) was used to calculate the binding parameters, which are shown in Table 1. The data indicate that the apparent dissociation constants are not significantly different while the apparent maximal surface concentration decreased significantly (p<0.001) when binding sites were blocked by free peptide.

TABLE 1

Specificity of the interaction between selected peptide of interest ASSLNIA and murine skeletal muscle homogenates

| Tissue homogenate | [a]$K_d$ (mg/ml) | [b]$M_{max}$ (ng/cm²) |
|---|---|---|
| Murine muscle | 0.28 ± 0.05 | 54.0 ± 4.0 |
| Blocked muscle[c] | 0.32 ± 0.05 | 34.4 ± 3.0 |

[a]The apparent dissociation constant, $K_d = 1/K_a$, was calculated from Hill plots.
[b]The apparent maximal surface concentration of protein, $M_{max}$, was estimated from an increase of the sensor voltage assuming that the bound layer has a density ~ 1 g/cm³.
[c]Murine muscle homogenate (50 mg/ml) was incubated with the free peptide (1 mg/ml) for 1 hour at room temperature.

Figure 4:
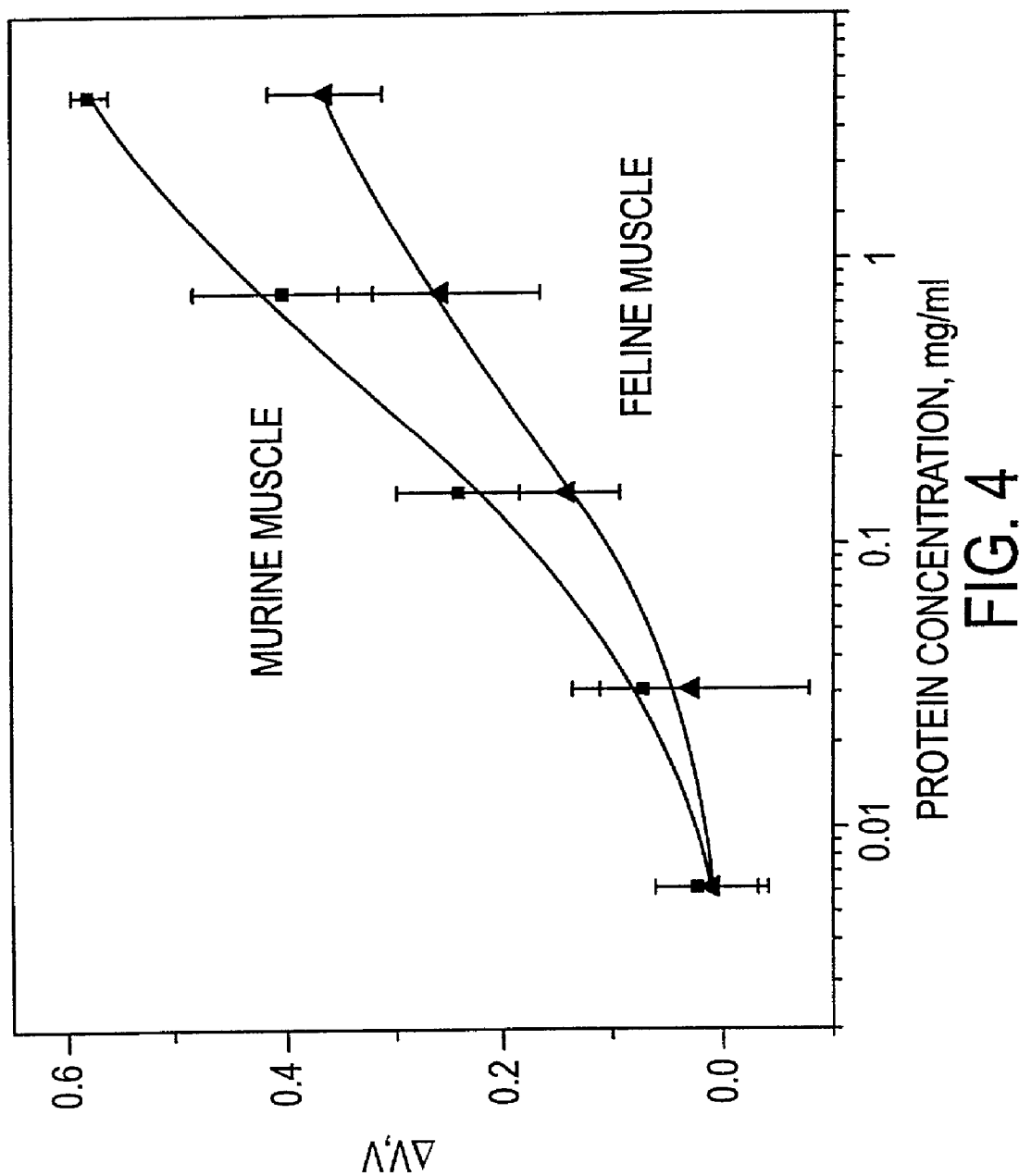
FIG. 4 shows the cross-species specificity of the peptide of interest selected for mouse muscle. Dose-response curves were obtained for LCD signal output in response to murine and feline skeletal muscle homogenates in the protein concentration range of $6.0 \times 10^{-3}$ to 3.8 mg/ml. Points represent experimental data for murine muscle (squares) and feline muscle (triangles), while smooth curves are the sigmoid fits to the experimental data ($\chi^2$=0.247 and $R^2$=0.999 for murine muscle; $\chi^2$=0.038 and $R^2$=0.998 for feline muscle).
Figure 5:
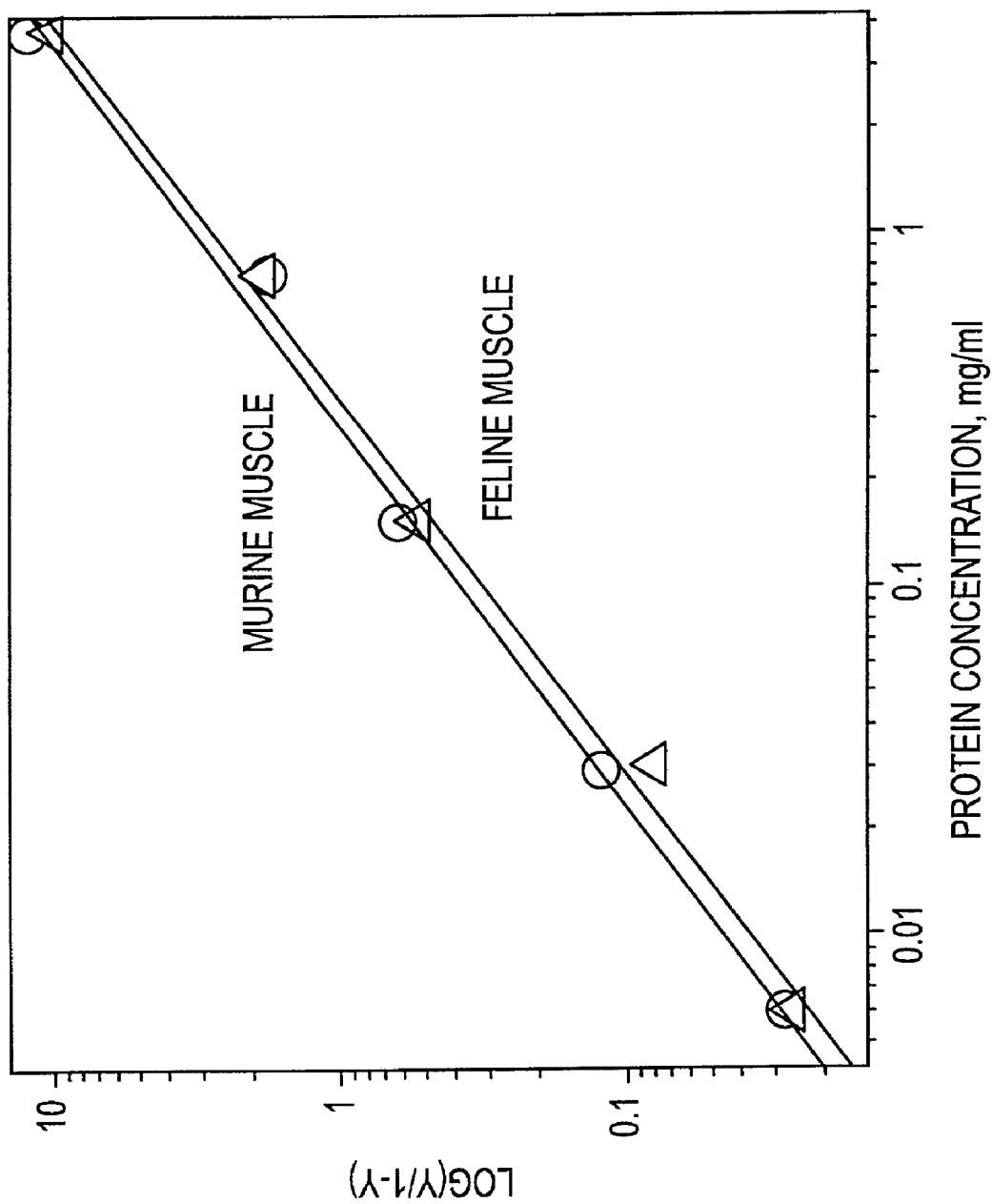
FIG. 5 shows Hill plots for the ratio of occupied and free peptide molecules on the sensor surface as a function of protein concentration for murine (upper line) and feline (lower line) muscle homogenates, respectively. Points represent experimental data. Lines represent the least square fit of equation (2) with coefficients shown in Table 2 (for both lines, R=0.997, SD=0.087 and p<0.0001).

While the amplitudes of the LSD signal output in response to the feline muscle homogenates were lower than those in response to murine muscle homogenate (FIG. 4), the positive correlation between LSD signal output and protein concentration for both homogenates indicates that the peptide has cross-species affinity. Analysis of Hill plots (FIG. 5) indicated that ligands from murine muscle had the same binding affinity to the peptide, but these ligands had a significantly higher maximal surface concentration (P<0.01) compared with parameters of ligands from feline muscle (Table 2).

TABLE 2

Interspecies specificity of ASSLNIA peptide to murine and feline skeletal muscle

| Tissue sample | [a]$K_d$ (mg/ml) | [b]$M_{max}$ (ng/cm²) | [c]Hill coefficient |
|---|---|---|---|
| Murine muscle homogenate | 0.32 ± 0.05 | 50.5 ± 3.0 | 0.92 ± 0.04 |
| Feline muscle homogenate | 0.37 ± 0.05 | 32.8 ± 2.0 | 0.93 ± 0.04 |

[a,b]Kd and M max were calculated as explained in the legend to Table 1.
[c]Hill coefficient was calculated by equation 2.

Dose response curves are in agreement with the Langmuir adsorption equation and the values of the Hill coefficient indicate that one binding site is needed to anchor a single bound molecule to the sensor surface Kuchel and Ralston (1988) *Theory and Problems of Biochemistry* (McGraw-Hill, New York). If we speculate that the target molecule of the surface antigen in murine myofibers is about 75–150 kD, then the apparent dissociation constant $K_d=0.28$ mg/ml (Table 1) falls in the range of ~1–2 μM. Dark field observations of the muscle homogenates used in these experiments revealed that average size of the tissue vesicles was about 1 micron. Taking into account that one 150 kD molecule occupies approximately 1000 Å² (Davies and Rideal (1963) *Interfacial Phenomena* (Academic Press, New York)), we can estimate that the mass of these molecules carried by a single vesicle takes only ~0.5% of the mass of the vesicle. This brings the $K_d$ down to ~5–10 nM. Finally, the assumption that not all molecules, but only a fraction of molecules on the vesicle surface can be specifically bound to the peptide lowers the apparent dissociation constant to a subnanomolar level (Vaughan et al. (1996) *Nat. Biotechnol.* 14: 309–314).

Figure 6:
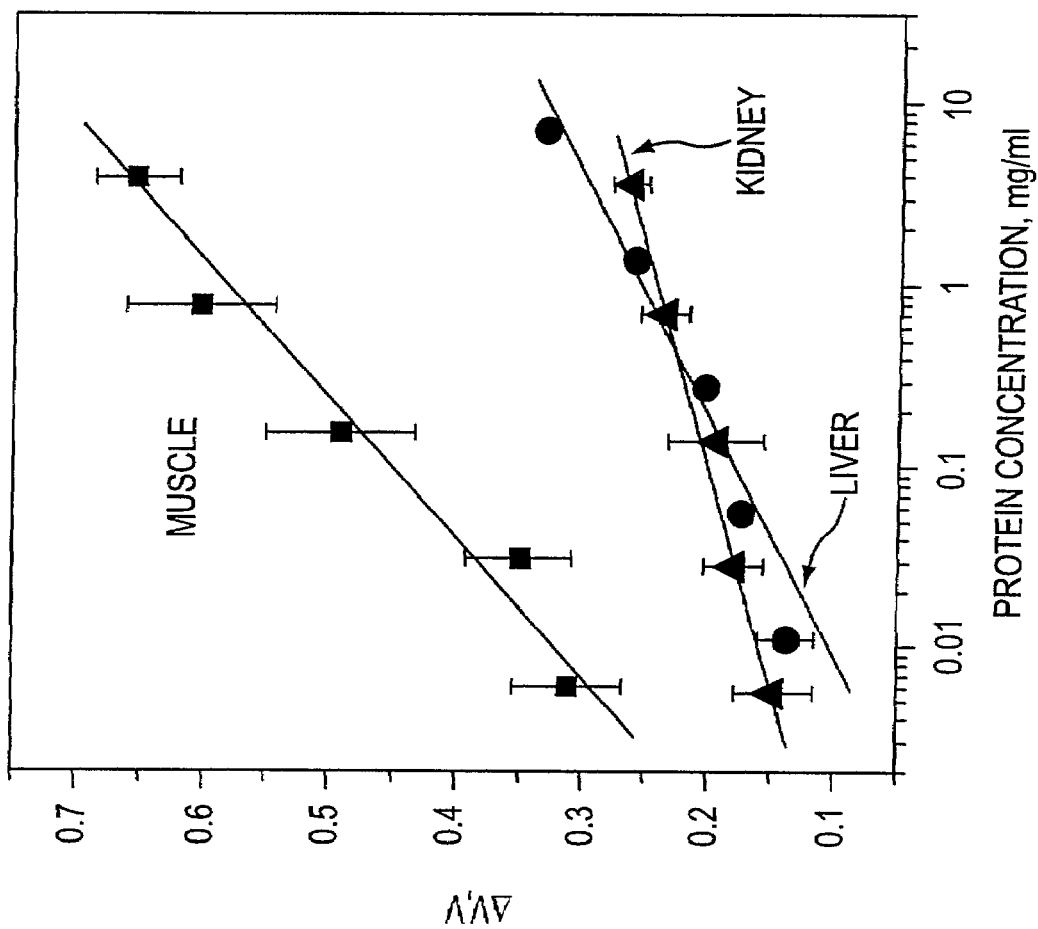
FIG. 6 shows selectivity of the muscle-specific peptide of interest. Dose-response plots were recorded with the LSD exposed to murine muscle homogenates, respectively. Points represent experimental data of 2–3 independent experiments (squares=muscle; triangles=kidney; circles=liver). Lines represent the least square fit of equation (3) with coefficients shown in the footnote of Table 3 (R=0.988, p<0.01, muscle; R=0.997, p<0.001, kidney; R=0.977, p<0.01, liver).

Binding selectivity of the Ligand Sensor Device. FIG. 6 shows the selectivity of the LSD. The upper line (squares) represents the dose response of the LSD to murine muscle homogenate. Two lower lines show the dose responses of the peptide sensor to the murine liver homogenate (circles) and kidney homogenate (triangle), respectively, within the same range of protein concentration. For any given concentration the LSD signal output for the muscle homogenate is greater than for liver or kidney homogenate. The voltage response ($\Delta V$) as a function of protein concentration (C) shown in FIG. 6 can be represented by the following empirical equation:

$$\Delta V = A + S \log C \quad (3)$$

where C is the protein concentration in the tissue sample, A is the constant, and S is the slope of the dose response dependence, defined as the sensitivity of the sensor (Pathirana et al. (1995) *Supramolecular Sci.* 2: 149–154).

As an example, the selectivity coefficient for any tissue homogenate to the muscle homogenate (K) can be estimated from the LSD signal output at different concentrations using a method similar to the matched potential method (Pathirana et al. (1995) *Supramolecular Sci.* 2: 149–154; Umezawa, ed. (1990) *CRC Handbook of Ion-Selective Electrodes: Selectivity Coefficients* (CRC Press, Boca Raton, Fla.). The selectivity coefficient (K) is defined as the activity ratio (R) of primary to interfering species ($\Delta C_{muscle}/\Delta C_{tissue}$) which gives the same response change at the same condition (Umezawa, ed. (1990) CRC *Handbook of Ion-Selective Electrodes: Selectivity Coefficients* (CRC Press, Boca Raton, Fla.)). By using the definition of the selectivity coefficient and equation (3), the following is derived:

$$R = \Delta C_{muscle}/\Delta C_{tissue} \quad (4)$$

$$K = R = S_{tissue}/S_{muscle} \text{ when } \Delta C_{muscle} \to 0 \quad (5)$$

where $S_{muscle}$ and $S_{tissue}$ are slopes of LSD signal output in response to muscle and another tissue (kidney, liver, or brain) homogenates, respectively (Pathirana et al. (1995) *Supramolecular Sci.* 2: 149–154).

Table 3 shows the sensitivity (S), the selectivity coefficient (K), and the activity ratio (R) for the LSD obtained for the experimental dose response data recorded for the muscle, kidney, brain, and liver homogenates, respectively.

TABLE 3

Selectivity of the muscle-specific peptide

| Tissue, Murine | (V/ decade) | Selectivity coefficient, K (relative units[a]) | Activity ratio, R (relative units[b]) | Phage selectivity[c] (relative units) |
|---|---|---|---|---|
| Muscle | 134 ± 20.0 | 1.0 | 1.0 | 1.0 |
| Kidney | 41.8 ± 7.0 | $(3.1 \pm 1.0) \times 10^{-1}$ | $(9.3 \pm 3.2) \times 10^{-5}$ | $1.1 \times 10^{-1}$ |
| Brain | 62.5 ± 16 | $(4.6 \pm 1.4) \times 10^{-1}$ | $(3.4 \pm 1.1) \times 10^{-3}$ | $0.5 \times 10^{-1}$ |
| Liver | 67.3 ± 6.0 | $(5.0 \pm 1.5) \times 10^{-1}$ | $(1.1 \pm 0.4) \times 10^{-3}$ | $0.7 \times 10^{-1}$ |

[a]Change of the output voltage is empirically described by the equation (3). The coefficient of selectivity for a certain tissue is calculated as the ratio of slopes $K = S_{tissue}/S_{muscle}$ (equation 5).
[b]The activity ratio $R = \Delta C_{muscle}/\Delta C_{tissue}$ (equation 4) was calculated using experimental equations: $\Delta V_{musce} = 0.593 + 0.134 \log C$; $\Delta V_{kidney} = 0.240 + 0.0418 \log C$; $\Delta V_{brain} = 0.296 + 0.0625 \log C$; $\Delta V_{liver} = 0.260 + 0.0673 \log C$ at the protein concentration in tissue homogenate equal to 0.01 mg/ml.
[c]Phage selectivity was calculated from the binding of ASSLNIA phage to skeletal muscles, brain, liver, and kidney compared to the binding of control wild-type phage in vivo experiments in mice (Samoylova and Smith (1999) *Muscle & Nerve* 22: 460–466).

As demonstrated by the data shown in Table 3, when the LSD is prepared with a peptide of interest selected on the basis of its in vivo muscle binding, there is a marked difference in LSD response for the muscle homogenate is observed over all other tissues. This is true even when the concentrations of other tissues substantially exceed the concentration of the muscle homogenate. For example, the activity ratio for the muscle and kidney homogenates at 0.01 mg/ml is equal to $9.3 \times 10^{-5}$. This means that more than 100 mg/ml of the kidney homogenate is needed to induce the same response as induced by only 0.01 mg/ml of the muscle homogenate. Thus, under these conditions, the LSD selectively prefers the ligand(s) in muscle homogenates to ligand(s) in kidney homogenates by factor of more than 10,000. The selectivity coefficient found for the LSD compares well with selectivity of phage carrying the peptide demonstrated in in vivo experiments (Table 3) (Samoylova and Smith (1999) *Muscle & Nerve* 22: 460–466). The acoustic wave sensor was successfully used for screening of phage display libraries (Hengerer et al (1999) *Biosens. Bioelectron* 14: 139–144). Here we report that the peptide specific to murine skeletal muscle found by screening of a phage display peptide library could be examined by the acoustic wave sensor system to determine the potential relevance of a ligand for a variety of species.

EXAMPLE 2

Preparation of a Ligand Sensor Device

The sensor is optionally prepared to be coupled to the peptide of interest by the deposition of a Langmuir-Blodgett film of monolayers which are prepared in the following manner. An extended description of such monolayers and their enhanced properties is set forth in copending application Ser. No. 09/452,968, filed Dec. 2, 1999.

Monolayers are prepared using a KSV 2200LB Langmuir-Blodgett apparatus (KSV-Chemical, Finland). The LB apparatus is thoroughly cleaned according to the following procedure. Prior to the monolayer preparation, the Teflon trough and the compression barrier of the LB apparatus are cleaned with either absolute ethanol or hexane. The edges of the trough, where contaminants can collect, are thoroughly cleaned. The trough is then filled with distilled water until a positive meniscus of about 2 mm formed at the trough edges. Contaminants floating at the air/water interface are removed by sweeping the compression barrier over the surface of the trough 3 times. Water that overflowed into the gutter is removed via a thin vinyl tube connected to a suction pump. The water in the trough is completely removed by suction immediately before filling the trough with the subphase. The enclosure doors are closed whenever possible to reduce contamination.

After cleaning the trough as described above, the trough is filled with 1.5 L of subphase solution comprising: 55.0 mM KCl, 4.0 mM NaCl, 1.0 mM $MgCl_2$, 0.1 mM $CaCl_2$ and 2.0 mM MOPS buffer in deionized doubly distilled water. The pH of the resultant solution is adjusted to 7.4 with 1 N KOH. The solution is then filtered, stored in a glass bottle and used within 2 days.

The trough thermostat is then adjusted to 20° C. When the subphase reaches this temperature (±0.1° C.), the subphase surface is cleaned by sweeping with the compression barrier. The overflow may be removed from the gutter by suction.

The Wilhelmy plate is cleaned by successive sonication in the following solvents for 1 minute each:
1. 2:1 chloroform/methanol
2. acetone
3. doubly distilled deionized water
4. absolute ethanol In order to ensure that the Wilhelmy plate is completely wettable, it may be sonicated in doubly distilled deionized water immediately before placement in the hang wire of the LB apparatus.

The pre-cleaned Wilhelmy plate is then suspended perpendicular to the subphase surface so that ⅓ of the plate is dipped in the subphase. In this arrangement, the $^{210}$Po air electrode may be kept 3 mm from the subphase surface and the Pt plate completely wetted. The compression barrier is fitted into the traverse fork and the surface pressure and the surface position may be zeroed using the DFC unit.

Formation of the Monolayers

A glass microscope slide (1×2 inch) is fixed to a sample holder that held the slide at a 165° angle to the subphase surface. The slide is then positioned so that its lower edge was just under the surface of the subphase. The peptide of interest is covalently coupled to liposomes according to the following procedure developed by Betageri et al. (1993) *J. Pharm. Pharmacol.* 45:48–53, the contents of which are incorporated by reference.

Synthetic L-α-1,2-dipalmitoyl-sn-glycerol-3-phosphocholine (DPPC) and maleimido phenyl butyrate phosphatidylethanolamine (MPB-PE) were obtained from Avanti Polar Lipids, Inc. (Alabaster, Ala.). Cholesterol, dicetyl phosphate and dithiothreitol (DTT) were purchased from Sigma Chemical Co. (St. Louis, Mo.). N-Succinimydyl-3-(2-pyridyldithio)propionate (SPDP) was purchased from Pierce, Rockford, Ill. The peptide of interest is identified as binding preferentially to human muscle when compared to its binding to bovine muscle. The peptide is synthesized in combination with a linker and purified by HPLC.

One ml of large, unilamellar liposomes are prepared as follows: 52.5 mg of DPPC, 33.5 mg of cholesterol, 19.9 mg of dicetyl phosphate and 10.0 mg of MPB-PE are placed in a 100 ml round bottom flask and dissolved in 10 ml chloroform and 25 ml tert-butanol. The solvents are evaporated in a rotary evaporator at 55° C., leaving a lipid film on the wall of the flask. Solvent traces are subsequently removed by leaving the flask in a vacuum desiccator overnight.

One ml of buffer A (110 mM KCl, 4 mM NaCl, 1 mM MgCl2, 0.1 mM CaCl2, 2 mM MOPS and adjusted to pH 7.4 with 1 N KCl) is added to the dry lipid film and vortexed until all the lipids were dispersed (approx. 15 min). The dispersed lipids are then subjected to 10 freeze (−80° C. for 30 minutes)/thaw (room temperature water for 10 minutes) cycles and then to 5 cycles of pressurized extrusion (at 500–600 psi) through a 0.4 μpore size polycarbonate filter (Nucleopore, Pleasanton, Calif.). The latter process is carried out in an extruder (Lipex Biomembranes, Inc. Vancouver, and BC, CANADA) maintained at 37° C. The resultant liposome solution is stored in the refrigerator until further use.

The peptide is then modified with the heterobifunctional reagent SPDP. 1.6 μl of 20 mM SPDP is added to 1 ml of PBS buffer containing 1 mg of peptide in a glass tube, resulting in a 5:1 molar ratio of SPDP:antibody. This reaction mixture is incubated for overnight at room temperature (21° C.). Unreacted SPDP is separated from the antibody by column chromatography using a Sephadex G-25 column equilibrated with 100 mM sodium acetate buffer (pH 4.5) acetate buffer (pH 4.5). Fractions are monitored by measuring the optical density at 280 nm. The SPDP is reduced to the thiol form by addition of DTT to a final concentration of 50 mM. After 20 minutes at room temperature the modified peptide was separated from the excess DTT by passing through a Sephadex G-25 column pre-equilibrated with 10 mM HEPES buffered saline, pH 8.0.

In order to conjugate the modified peptide to liposomes, 100 μl of the antibody modified with SPDP is mixed with 100 μl of the liposome solution and incubated at room temperature for 24 hours with constant stirring under a nitrogen stream. Separation of the conjugated liposomes from the noncoupled peptide is accomplished as follows. 200 μl of the conjugated liposome solution is aliquoted into a 10 ml centrifuge tube and 1.5 ml of 40% (w/v) metrizamide is layered over the liposome mixture. This was followed by layers of 2.5 ml 20% (w/v) metrizamide and 0.5 ml PBS. This gradient was centrifuged for 30 minutes at 34,000 rpm (143,000 g). On centrifugation, the liposomes migrate out of the lower layer to the interface between the second medium layer and the buffer layer on the top of the gradient. The unbound peptide remains at the bottom of the gradient. The fraction containing the peptide-liposome conjugates is collected, diluted with the buffer A to a phospholipid concentration of 1 mg/ml and stored in the refrigerator until use as the spreading solution for monolayer preparation.

Monolayers are prepared and transferred to sensor substrates. A solution of the phospholipid is mixed well and then, using a micropipette, 100 μl is deposited drop-wise onto the surface of the microscope slide at a rate of about 0.1 ml/minute. The microscope slide is next immersed in the subphase so that the area of the slide covered by the antiserum was completely submersed. The slide is then withdrawn completely from the subphase solution. After 10 minutes, the monolayer is compressed to a surface pressure of 23 mN/m. The pressure is determined by analysis of surface pressure-surface area isotherms.

LB Film Deposition

The Maxtek quartz crystals are cleaned according to the following procedure. The substrates (sensors or crystals) are placed in 50% nitric acid for 2 days and then rinsed thoroughly in distilled water to remove any traces of nitric acid. The substrates are then dried in air and stored in covered containers until further use. Before spreading the monolayer as described above, the substrate is fixed to a sample holder and placed in the subphase so that the area to be covered by the monolayer was under the subphase surface. Monolayers are then added to the substrate by standard techniques or as set forth in copending application Ser. No. 09/452,968, filed Dec. 2, 1999.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method for evaluating the affinity of one or more ligands for a peptide of interest, comprising the steps of:
   a) identifying said peptide of interest;
   b) preparing a sensor to be coupled to said peptide by depositing a Langmuir Blodgett film on said sensor, wherein said Langmuir-Blodgett film is prepared from monolayers formed from a method comprising the steps of:
      i) providing a composition comprising at least one amphiphilic compound, wherein said amphiphilic compound is a phospholipid which has been coupled to said peptide of interest and said composition contains not more than 25% of a volatile organic solvent;
      ii) immersing one end of a wettable planar surface into an aqueous subphase, wherein said planar surface forms an angle of about 90–170 degrees to an air/liquid interface of said subphase, and said subphase comprises at least one monovalent cation and at least one bivalent cation;
      iii) delivering said composition at a rate of about 0.02–4.0 ml per minute to said planar surface to form a monolayer; and
      iv) compressing said monolayer to an optimal surface pressure;
   c) depositing said Langmuir-Blodgett film of step b) to said sensor;
   d) quantifying a signal output from said sensor;
   e) exposing said sensor to one or more ligands; and
   quantifying a signal output from said sensor after step e) and comparing to the previously obtained signal from step d) to thereby evaluate the affinity of said one or more ligands for said peptide of interest.

2. The method of claim 1, wherein said amphiphilic compound is a phospholipid which has been covalently coupled to a peptide of interest.

3. The method of claim 2, wherein said peptide of interest comprises the amino acid sequence set forth in SEQ ID NO: 1.

4. The method of claim 1, wherein said sensor comprises a piezoelectric crystal.

5. The method of claim 4, wherein said sensor is an acoustic wave sensor.

6. The method of claim 1, wherein the step of preparing said peptide to be coupled to said sensor comprises biotinylation of said peptide.

* * * * *

UNITED STATES PATENT AND TRADEMARK OFFICE
CERTIFICATE OF CORRECTION

PATENT NO. : 7,138,238 B2  Page 1 of 1
APPLICATION NO. : 10/068570
DATED : November 21, 2006
INVENTOR(S) : Vodyanoy et al.

It is certified that error appears in the above-identified patent and that said Letters Patent is hereby corrected as shown below:

Column 1,

Line 37: "The" begins a new paragraph

Column 24,

Line 37: Insert --f)-- at beginning of line

Signed and Sealed this

Twenty-second Day of May, 2007

JON W. DUDAS
*Director of the United States Patent and Trademark Office*